United States Patent [19]

Delente et al.

[11] 4,081,432
[45] Mar. 28, 1978

[54] METHOD OF SEPARATING A FACTOR IX PREPARATION FROM PLASMA USING ETHYLENE-MALEIC ANHYDRIDE POLYMERS

[75] Inventors: Jacques J. Delente, University City; Richard A. Schoenfeld, St. Louis, both of Mo.

[73] Assignee: Monsanto Company, St. Louis, Mo.

[21] Appl. No.: 818,920

[22] Filed: Jul. 25, 1977

[51] Int. Cl.$^2$ .............................................. C07G 7/00
[52] U.S. Cl. .................. 260/112 B; 424/101; 424/177
[58] Field of Search .................. 260/112 B; 424/101, 424/177

[56] References Cited

U.S. PATENT DOCUMENTS

| | | | |
|---|---|---|---|
| 3,554,985 | 1/1971 | Fields et al. | 260/78 X |
| 3,555,001 | 1/1971 | Wallis et al. | 260/112 B |
| 3,682,881 | 8/1972 | Fekete et al. | 260/112 B |
| 3,717,708 | 2/1973 | Wada et al. | 260/112 B |
| 3,920,625 | 11/1975 | Andersson et al. | 260/112 B |

*Primary Examiner*—Howard E. Schain
*Attorney, Agent, or Firm*—Scott J. Meyer; James W. Williams, Jr.

[57] ABSTRACT

A Factor IX preparation is separated from plasma by selective adsorption of Factors II, IX and X to the substantial exclusion of Factors VII and VIII with 0.025–0.1% by weight of a water-insoluble, cross-linked polyelectrolyte copolymer of ethylene and maleic anhydride containing pendant diloweralkylaminoloweralkyl functional groups.

6 Claims, No Drawings

METHOD OF SEPARATING A FACTOR IX PREPARATION FROM PLASMA USING ETHYLENE-MALEIC ANHYDRIDE POLYMERS

BACKGROUND OF THE INVENTION

This invention relates to blood fractionation and more particularly to the separation of a blood coagulation Factor IX preparation from plasma by the selective adsorption of Factors II, IX and X.

The process of blood coagulation is a complicated physiological activity that involves the interaction of numerous substances found in normal whole blood. It is known that certain factors associated with the blood coagulation mechanism are absent or seriously deficient in certain individuals. In those patients suffering from classical hemophilia, antihemophilic factor A (AHF, Factor VIII) is deficient. In those patients afflicted with hemophilia B, plasma thromboplastin component (PTC, Factor IX) is missing from the blood.

Several other factors which are important in the coagulation mechanism are Factors II, VII and X. As with Factors VIII and IX, these other factors also are deficient or absent in certain individuals. Factors II, VII and X are usually associated with Factor IX in the fractionation of blood plasma into various fractions, and a concentrate of these four factors has come to be known as the prothrombin complex.

In the development of modern blood banking programs involving the collection and storage of large quantities of blood and blood components, the establishment of adequate preservation systems is critical. Since World War II it has been common practice to collect blood in a solution of citric acid, sodium citrate and dextrose known as ACD blood. The problem of preserving blood is much simplified, however, when it is reduced to preservation of various blood components since it is easier to meet the environmental requirements of the separate components than of whole blood.

Moreover, it is wasteful and even detrimental to the patient to administer more blood components than required. Thus, the hemophiliac needing certain blood coagulation factors ideally should be given only those factors required or at least a purified concentrate of these factors containing a reduced level of unneeded factors.

The fractionation of blood to obtain blood coagulation Factors VIII and IX and the prothrombin complex is well known. Most fractionation methods require the separation of Factor VIII from the plasma or other starting material prior to the separation of Factor IX or the prothrombin complex. For example, Factor VIII is frequently first separated from plasma as a cryoprecipitate or by precipitation with glycine or polyethylene glycol as described in U.S. Pat. Nos. 3,631,018 and 3,652,530 and references cited therein.

Various prior methods of blood fractionation for the preparation of the prothrombin complex include the barium sulfate adsorption method described by Fowell in U.S. Pat. No. 2,999,791 and the tricalcium phosphate adsorption method disclosed by Soulier et al, *La Presse Medicale* 72, 1223-28 (1964). Tullis discloses the use of DEAE-cellulose ion exchanger for the production of a prothrombin complex, *New England Journal of Medicine* 273, 667-74 (1965) while the corresponding use of DEAE-Sephadex is described by Wado and Mozen in U.S. Pat. No. 3,717,708. Andersson et al in U.S. Pat. No. 3,920,625 further describe the use of DEAE-Sephadex specifically for the preparation of Factor IX concentrates. Use of polyethylene glycol for the production of prothrombin complex is taught by Fekete and Shanbrom in U.S. Pat. Nos. 3,560,475 and 3,682,881. Aluminum hydroxide and other such gel materials also are known as useful in the concentration of prothrombin complex factors as seen from Bidwell, U.S. Pat. No. 2,867,567.

As distinguished from all of the foregoing methods, in the present invention a Factor IX preparation is separated from plasma such that it also contains Factors II and X but not Factor VII which is usually contained in the prothrombin complex concentrates of the prior art. Moreover, the Factor IX preparation of this invention advantageously can be separated from the plasma prior to the separation of Factor VIII.

BRIEF SUMMARY OF THE INVENTION

In accordance with the present invention, a Factor IX preparation containing Factors II, IX and X is separated from liquid plasma with a water-insoluble, cross-linked polyelectrolyte copolymer of ethylene and maleic anhydride containing pendant diloweralkylaminoloweralkyl functional groups. By use of the polyelectrolyte copolymer at a relatively low concentration of from about 0.025% to about 0.1% by weight of the plasma and a pH of from about 7.5 to about 8.5, a Factor IX preparation containing Factors II, IX and X surprisingly is selectively adsorbed by the polyelectrolyte copolymer to the substantial exclusion of Factors VII and VIII which are unadsorbed and remain in the liquid plasma.

If desired, the adsorbed Factor IX preparation can then be eluted from the polyelectrolyte by washing with an aqueous solution of a physiologically acceptable salt such as NaCl, for example a solution of about one to three molar NaCl. The elution preferably is carried out at a pH of from about 5.5 to about 6.5 although higher pH's also can be used.

DETAILED DESCRIPTION OF THE INVENTION

The starting plasma used in the fractionation method of this invention is generally obtained fresh frozen. This plasma should be thawed before fractionation with the polyelectrolyte copolymer, preferably by heating to a temperature of at least about 35° C. The appropriate polyelectrolyte copolymer can then be admixed with the plasma at a concentration of from about 0.025% to about 0.1% and preferably about 0.035% to about 0.05%, and the pH adjusted to a range of from about 7.5 to about 8.5. The mixture is stirred for a suitable time, for example at least about 10 minutes, during which time the Factor IX preparation is selectively adsorbed by the polyelectrolyte copolymer and the remaining liquid plasma is made deficient in Factors II, IX and X.

In general, the water-insoluble, cross-linked polyelectrolyte copolymers employed in this invention are copolymers of ethylene and maleic anhydride containing pendant diloweralkylaminoloweralkyl functional groups. By the term "loweralkyl" is meant an alkyl having from about 1 to about 4 carbon atoms.

The base copolymer of ethylene and maleic anhydride (EMA) can be prepared, for example, by reacting ethylene and maleic anhydride in the presence of a peroxide catalyst in a suitable solvent. The copolymer will preferably contain substantially equimolar quantities of the ethylene residue and the anhydride residue.

The base EMA copolymer can be reacted with a loweralkyliminobisloweralkylamine which has two primary amine groups and leads to a cross-linked EMA copolymer. The desired pendant diloweralkylaminoloweralkyl functional groups can then be incorporated into the cross-linked copolymer by reaction of diloweralkylaminoloweralkylamine with part or all of the remaining anhydride groups of the EMA polymer. The polyelectrolyte copolymer also desirably is converted to the HCl salt form to provide better handling characteristics. Further details on the preparation of these polyelectrolyte copolymers can be had by reference to the disclosure in U.S. Pat. No. 3,554,985 which is incorporated herein by reference. Use of these polyelectrolyte copolymers in blood fractionation is described in U.S. Pat. No. 3,555,001.

A preferred diloweralkylaminoloweralkyl functional group is dimethylaminopropyl and a preferred cross-linking agent is methyliminobispropylamine.

A preferred polyelectrolyte copolymer for use in this invention contains about five methyliminobispropylamine cross-linking groups and about 90 pendant dimethylaminopropylamine functional groups per 100 maleic anhydride units in the EMA copolymer.

Other cross-linking agents, for example, divinylbenzene and ethylene diamine, and other functional groups, for example, dimethylaminoethyl and diethylaminobutyl, also can be used in the polyelectrolyte copolymers which are employed in the method of separating the Factor IX preparation herein.

Following the adsorption of the Factor IX preparation, the Factor VIII remaining in the plasma solution can be further concentrated and recovered by known techniques. A preferred method is disclosed in the commonly assigned copending application of Fields and Slocombe, Ser. No. 818,918, entitled "Non-Activating Polyelectrolytes for Separation of Blood Coagulation Factors", filed simultaneously herewith. The adsorbed Factor IX preparation can be conveniently recovered by elution from the polyelectrolyte copolymer by washing with an aqueous solution of NaCl having a molarity of from about one to about three.

In a preferred embodiment of the invention, about 0.035% by weight of the polyelectrolyte copolymer containing about five methyliminobispropylamine cross-linking groups and about 90 dimethylaminopropylamine functional groups per 100 maleic anhydride units in the EMA copolymer is employed for selective adsorption of the Factor IX preparation at a pH of about 8. The adsorbed Factor IX preparation is then eluted from the polyelectrolyte copolymer by washing with 1.7 molar NaCl at pH 6. The eluant can then be dialyzed against 0.1 molar NaCl at 4° and freeze dried for storage.

The following examples will further illustrate the invention although it will be appreciated that the invention is not limited to these specific examples.

EXAMPLE I

In this example, the polyelectrolyte copolymer consisted of the reaction product of substantially equimolar parts of ethylene and maleic anhydride (EMA) cross-linked with methyliminobispropylamine (MIBPA) and then further reacted with dimethylaminopropylamine (DMAPA) such as to provide about five MIBPA cross-linking groups and about 90 DMAPA pendant groups per 100 maleic anhydride units in the EMA copolymer and converted to the HCl salt form. One liter of normal human plasma was adjusted to pH 8 with 1 molar NaOH and 0.35 grams of the aforesaid polyelectrolyte copolymer was added thereto and the mixture was stirred for 20 minutes. The mixture was then filtered and the filtrate was retained as a Factor IX depleted plasma. The filter cake was washed with distilled water to remove entrained protein.

A Factor IX preparation containing Factors II, IX and X was then eluted from the polyelectrolyte copolymer by washing with 25 ml. of 1.7 molar NaCl at pH 6.0 (the pH being adjusted with 0.1 molar citric acid) for 20 minutes. The copolymer slurry was then filtered and the filtrate was retained as the desired Factor IX preparation. In a series of seven one-liter replicate fractionations using the above procedure, an average of 483 ± 48 units of Factor IX per liter were obtained having a purification index of 178 ± 33. One unit of Factor IX is defined as the amount of said factor in one ml of pooled normal whole plasma. The purification index is calculated as the ratio of the amount of total protein in the starting plasma to the amount of total protein in the final Factor IX preparation multiplied by the ratio of the units of Factor IX in the final Factor IX preparation to the units of Factor IX in the starting plasma.

EXAMPLE 2

Using 0.4 mg/ml of the polyelectrolyte copolymer of Example 1 for admixture with normal human plasma for 20 minutes at pH 7.4 to separate a factor IX preparation, as in Example 1, the adsorption of Factors II, VII, VIII, IX and X was measured with the following results:

| Factor | % Adsorbed* |
|--------|-------------|
| II     | 83          |
| VII    | 0           |
| VIII   | 5           |
| IX     | 96          |
| X      | 83          |

*based on amount in starting plasma

These results show a high selectivity for adsorption of Factors II, IX and X to the substantial exclusion of Factors VII and VIII based on the corresponding amounts of these factors in the starting plasma.

Conventional one-stage assays were used for determining the coagulation factors in the foregoing examples. The one-stage assay system for Factor VIII sold commercially by Dade Division of American Hospital Supply Corporation was employed in these examples. This assay system is based on the activated partial thromboplastin time (PPT) used to determine deficiencies in factors necessary for the intrinsic method of clot formation. The PTT test was devised by Brinkhous and co-workers and reported in *J. Lab. Clin. Med.* 41, 637 (1953). In these assays for the various coagulation factors, the unknown sample was reacted with a partial thromboplastin reagent and the appropriate factor-deficient substrate plasma which did not contain the factor to be determined, and the time for clotting was observed. The partial thromboplastin reagent contains crude cephalin obtained from rabbit brain which is known to clot normal plasma faster than it clots hemophilic plasma. Such reagents are well-known and described, for example, in U.S. Pat. Nos. 3,395,210, 3,486,981 and 3,522,148.

Various other examples will be apparent to the person skilled in the art after reading the disclosure herein without departing from the spirit and scope of the invention. It shall be understood that all such examples are included within the scope of the appended claims.

What is claimed is:

1. A method of separating a Factor IX preparation from plasma comprising contacting liquid blood plasma at a pH of from about 7.5 to about 8.5 with from about 0.025% to about 0.1% by weight of the plasma of a water-insoluble, cross-linked polyelectrolyte copolymer of ethylene and maleic anhydride containing pendant diloweralkylaminoloweralkyl functional groups whereby Factors II, IX and X are selectively adsorbed by the polyelectrolyte copolymer to the substantial exclusion of Factors VII and VIII which are unadsorbed and remain in the liquid plasma.

2. The method of claim 1 in which the diloweralkylaminoloweralkyl functional group is dimethylaminopropyl.

3. The method of claim 1 in which the copolymer of ethylene and maleic anhydride is cross-linked with methyliminobispropylamine.

4. The method of claim 1 in which the polyelectrolyte copolymer contains about five methyliminobispropylamine cross-linking groups and about 90 dimethylaminopropyl pendant groups per 100 maleic anhydride groups.

5. The method of claim 1 in which the adsorbed Factor IX preparation is eluted from the polyelectrolyte copolymer by washing with an aqueous solution of NaCl having a molarity of from about one to about three.

6. The method of claim 1 in which the concentration of the polyelectrolyte copolymer is from about 0.035% to about 0.05% by weight of the plasma and said polyelectrolyte copolymer contains about five methyliminobispropylamine cross-linking groups and about 90 dimethylaminopropyl pendant groups per 100 maleic anhydride groups.

* * * * *